United States Patent

Garito et al.

[11] Patent Number: 6,004,318
[45] Date of Patent: Dec. 21, 1999

[54] ELECTROSURGICAL ELECTRODE FOR TREATING GLAUCOMA

[76] Inventors: Jon C. Garito; Alan G. Ellman, both of 1135 Railroad Ave., Hewlett, N.Y. 11557

[21] Appl. No.: 09/005,573

[22] Filed: Jan. 12, 1998

Related U.S. Application Data

[63] Continuation of application No. 08/705,599, Aug. 30, 1996, Pat. No. 5,755,716.

[51] Int. Cl.⁶ .................................................. A61B 17/36
[52] U.S. Cl. .................................. 606/41; 606/40; 606/49
[58] Field of Search .................................. 606/34, 37, 39, 606/40, 41, 45, 49, 166, 170

[56] References Cited

U.S. PATENT DOCUMENTS

| 5,105,808 | 4/1992 | Neuwirth et al. | 606/27 |
| 5,197,962 | 3/1993 | Sansom et al. | 606/45 |
| 5,380,320 | 1/1995 | Morris | 606/40 |

*Primary Examiner*—John P. Leubecker
*Assistant Examiner*—Bryan K. Yarnell

[57] ABSTRACT

An electrosurgical coagulation electrode to accomplish direct cyclocoagulation for treating glaucoma. To this end, the electrode is a flat, thin, slightly-flexible electrically-conductive member coated with an electrically-insulating coating over all but a small exposed area at one surface of the electrode tip. With this novel shape, it becomes possible to effect coagulation where desired in a relatively simple manner.

20 Claims, 2 Drawing Sheets

6,004,318

ELECTROSURGICAL ELECTRODE FOR TREATING GLAUCOMA

This application is a continuation of application Ser. No. 08/705,599, filed Aug. 30, 1996, now U.S. Pat. No. 5,755,716.

This invention relates to an electrosurgical instrument for treatment of glaucoma and, in particular, to an electrosurgical electrode for relieving pain and slowing progression of the disease of glaucoma, especially end-stage glaucoma, and to the procedure for treating glaucoma with electrosurgery.

BACKGROUND OF THE INVENTION

Glaucoma is an eye disease characterized by increased intraocular pressure, which eventually causes degeneration in the optic nerve head. In its end-stage, it is also extremely painful. One known surgical procedure uses an expensive laser to effect entry into the suprachoroidal space to relieve the pressure.

SUMMARY OF THE INVENTION

An object of the invention is an improved treatment for glaucoma using an electrosurgical instrument.

We have invented a novel electrode for use in an electrosurgical glaucoma procedure. This electrosurgical procedure using our novel electrode enables physicians to offer to patients a treatment for relieving pain and possibly slowing the disease that is efficiently performed, easily learned and thus performed at a significantly reduced cost, with less tissue damage compared to procedures done heretofore, and, most important, with better control over the depth of the treatment.

The procedure is based on forming an appropriate incision to expose the choroid and relieve the intraocular pressure, followed by electrosurgical coagulation using our novel electrode to accomplish direct cyclocoagulation. To this end, the electrode of the invention comprises a flat, thin, slightly-flexible electrically-conductive member coated with an electrically-insulating coating over all but a small exposed area at the surface of the electrode tip. With this novel shape, it becomes possible to effect coagulation where desired in a relatively simple manner. It should be recognized that in advanced glaucoma, the principal goal is pain relief with small hope of improved vision, and the treatment described with the electrosurgical electrode of the invention offers a simple inexpensive treatment.

The active exposed tip is supported by structure that is completely electrically-insulated to avoid damage to surrounding tissue, and to allow the physician to use these inactive insulated parts to help position and guide the active tip, which is the only part capable of treating tissue, during the surgical procedure.

The electrosurgical procedure has the important advantage of coagulating the cut tissue causing minimum bleeding. It is preferred that the electrosurgical currents used be above 2 MHZ, and preferably above 3 MHZ. At these high frequencies, commonly referred to as radiosurgery, the action is limited to the exposed tip of the electrode, which is primarily responsible for only small lateral heat spread and thus less damage to neighboring cell layers.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described the preferred embodiments of the invention, like reference numerals or letters signifying the same or similar components.

BRIEF DESCRIPTION OF THE DRAWINGS

In the drawings:

FIGS. 4 and 4A are perspective views showing how the electrosurgical instrument according to the invention can be used in glaucoma treatment.

DETAILED DESCRIPTION OF THE PREFERRED EMBODIMENTS

Figure 2:
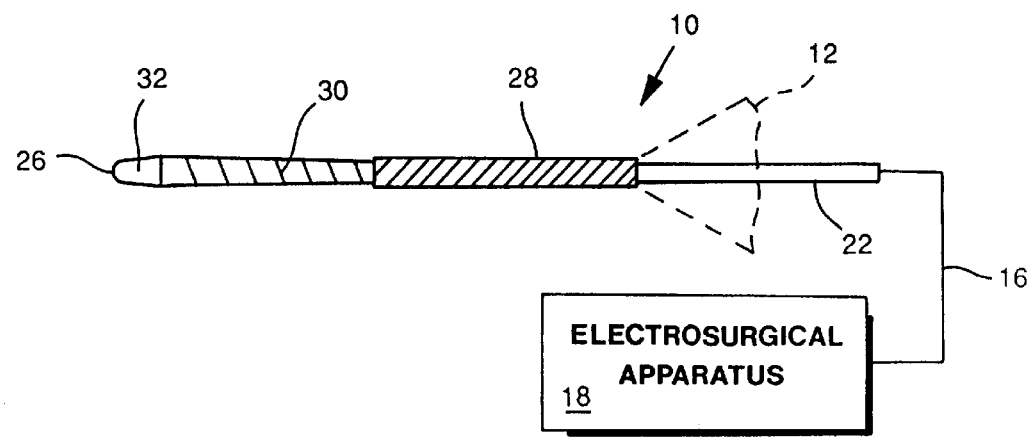
FIGS. 2 and 3 are plan views of opposite sides of the completed electrosurgical instrument in accordance with the invention shown connected to electrosurgical apparatus.
Figure 3:
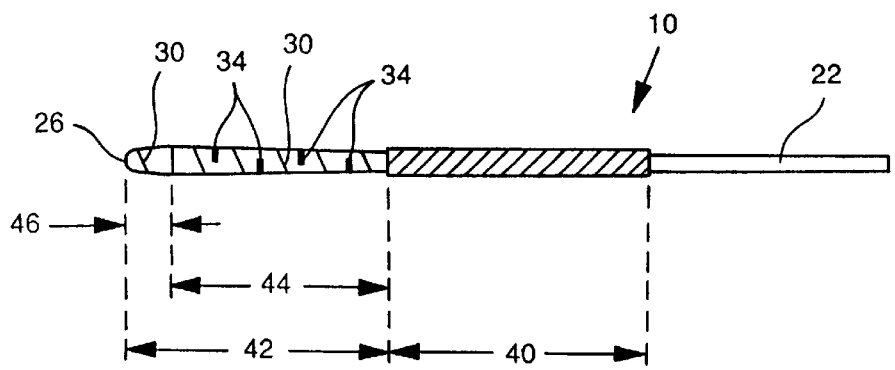

FIG. 2 and 3 illustrate a preferred form of the novel electrosurgical instrument 10 of the invention. It comprises an elongated conventional handpiece 12 (only the collet end is shown in phantom) of electrically-insulating material having a central electrically-conductive tube or conductor (not shown) extending throughout its length and connected at its end to a cable 16 which is connected in the conventional manner to conventional electrosurgical apparatus 18. As an example only, the electrosurgical apparatus can be model AAOP Surgitron FFPF available from Ellman International, Inches of Hewlett, N.Y. The Ellman equipment is preferred due to its high operating frequency, typically above 2 MHZ, preferably above 3 MHz. This particular apparatus provides electrosurgical currents at 3.8 MHZ.

At the opposite end of the handpiece 12 is mounted the electrosurgical electrode 10 which comprises an electrically-conductive straight axial brass or bronze rod 22 which is exposed at the right end for being received in the handpiece collet 12 electrically connected to the electrically-conductive cable 16. At the left end, the rod 22 is flattened to form a thin flat slightly-flexible strip 24. The distal end of the electrode comprises a rounded tip 26. The center region is coated on both sides with an electrically-insulating coating 28, for example of rubber or plastic, which may be of any desired thickness. The left end is coated with a very thin electrically-insulating coating 30 of, for example, baked "Teflon". For ease of understanding, the coatings are shown hatched in the plan views of FIGS. 1–3.

Figure 1:
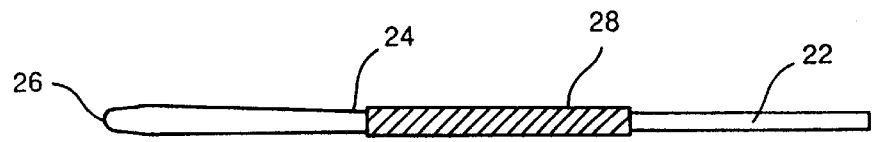
FIGS. 1 is a plan view of one form of electrosurgical instrument in accordance with the invention, before manufacture completion.

FIG. 1 shows the electrode 10 after the thicker coating 28 is applied but before the thinner coating 30 is applied, which is shown in FIGS. 2 and 3. The latter are plan views of opposite sides of the completed electrode. As will be noted, on the side shown in FIG. 3, the electrically-insulating coating 30 extends the full length from the thicker coating 28 to the rounded tip 26. On the opposite side, shown in FIG. 2, the coating extends only part of the distance, leaving exposed and thus electrically active a small surface region 32 adjacent the rounded tip 26 on only one side of the flat electrode. In addition, on the fully coated side shown in FIG. 3, depth marks 34 are provided at uniform intervals of, for example, 3 mm apart.

For illustrative purposes, the thickness (the dimension perpendicular to the plane of the drawing) of the flat electrode 10 at the small surface region 32, including the coating 30, is about 0.005–0.009 inches, preferably about 0.006 inches. The width (the vertical dimension in the plane of the drawing) of the electrode 10, including the coating 30, is about 0.07–0.09 inches, preferably about 0.0078 inches. The overall length (the horizontal dimension in the plane of the drawing) of the electrode 10 is about 2.25 inches. The length 40 is about 0.8 inches. The more important dimensions are that of the thinly coated left end of the electrode 10. The length dimension 42 is about 0.6–0.9 inches, preferably about 0.783 inches, and the length dimensions 44 and 46 are, respectively, about 0.6–0.7 inches, preferably about 0.63 inches, and about 0.1–0.2 inches, preferably about 0.157 inches. The electrical insulation of the thinner coating 30 has a thickness in the range of about 0.002–0.008 inches. For the examples given, the length 46 of the bare part of the working end 24 is approximately 1/10–1/3 of the full length 42.

Figure 4:
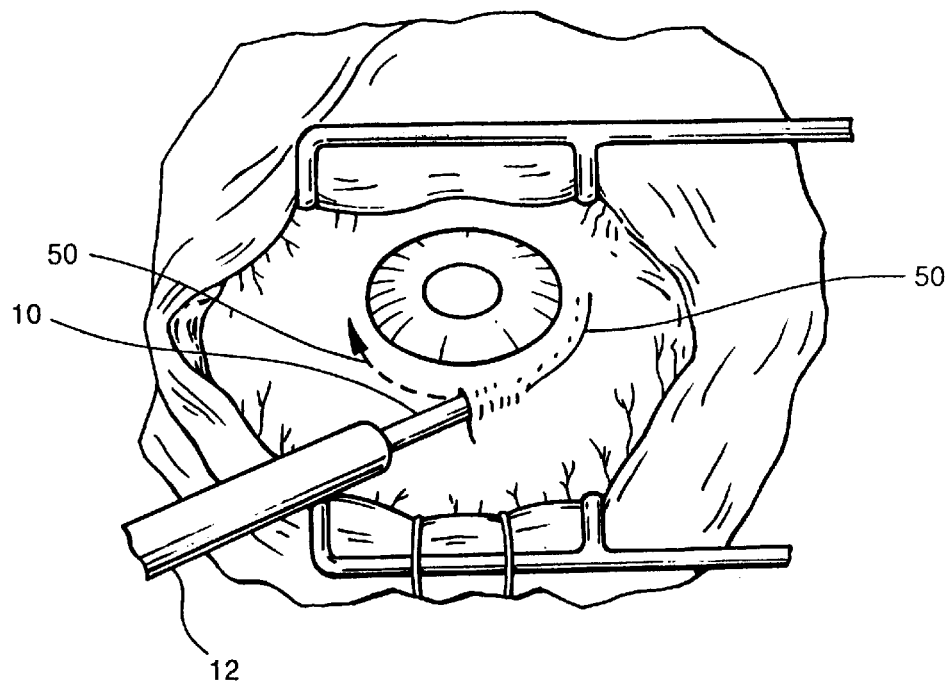
Figure 4:
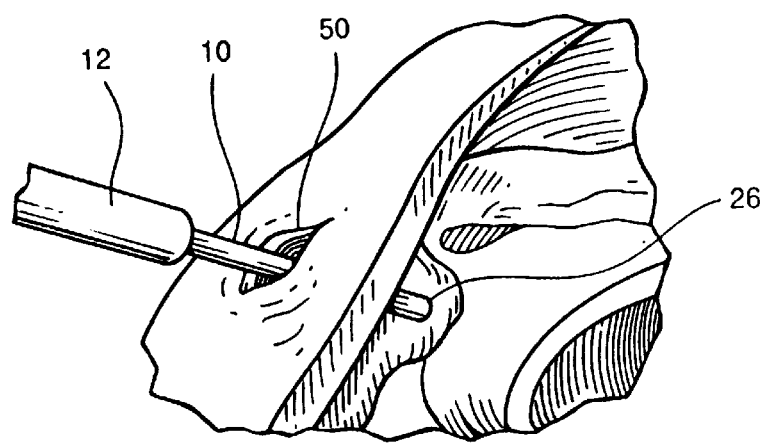

The actual procedure is as follows. After the usual local anesthesia, tractors are applied to expose the patient's eye, and an incision made along the 12 o'clock meridian shown at 50 in FIG. 4. The incision was carried down to expose the choroid. The electrosurgical apparatus previously identified was set at a power setting of "6", using the partly rectified waveform. The electrode in the handpiece 12 was then inserted into the scleral incision over the ciliary body with the exposed end 32 applied directly to the outer surface of the ciliary body and facing down leaving the back side shown in FIG. 3 visible to the surgeon. At the first mark 34, the apparatus was energized for about 1 second and then shut off, then the electrode was advanced 3 mm into the incision to the second mark 34 and the apparatus again reenergized for 1 second, and the process repeated until the final mark was reached. At that point, the electrode was retracted in 3 mm steps, each time being energized for about 1 second as each mark was reached until the electrode was completely removed. The total depth of treatment was about 18 mm, during which when advancing and retracting the energized electrode introduced radiofrequency currents via the exposed tip 32 at the contacted tissue causing coagulation of blood vessels severed during the incision. Post operative treatment was conventional. Timing the electrosurgical burns as evenly as possible was found desirable. The merit of the treatment is that, by applying the thin electrode with its exposed small surface region directly to the outer surface of the ciliary body in the suprachoroidal space, coagulation of the choroidal tissue without affecting the sclera can easily be achieved with a relatively inexpensive instrument.

The rounded tip 26 offers the advantage of making it easier to get into the scleral wound, and the marks 34 on the back side visible to the physician provide an easy means to determine how deep the electrode has penetrated. The electrode substrate 24 of bendable brass allows the physician to slightly curve the electrode (perpendicular to its plane) as needed for greater control over the penetration angle. Also connected to the electrosurgical apparatus 18 is the usual indifferent plate (not shown) which during use is in contact with the patient's body. When the electrosurgical apparatus 18 is energized, high frequency electrosurgical currents are generated which are coupled by way of the cable 16 and electrically-conductive rod 22 to the active surface region 32. The physician, in the usual way, holds the handpiece 12 while applying the active working end of the electrode to the desired area of the patient to be treated. The handpiece 12 is completely electrically-insulated. The insulating coatings 28 and 30 are essential to prevent accidental burning or other tissue damage by the sides of the electrode as the instrument is manipulated.

For completeness' sake, attention is directed to U.S. Pat. No. 4,517,975 which describes an electrosurgical electrode for nail matrisectomy. The electrode comprises a short spade-shaped end with one side completely covered with an electrically-insulating coating. The active end is less than about ½ inches as it need be inserted only a short distance under the nail. Moreover, the entire bottom surface is exposed and thus active, and no markings on the back side are needed since the penetration depth is less critical and the burning does not occur at spaced intervals. In the present invention, the depth penetration includes the entire length 42, whereas only a small part 32 of the front side is uncoated, so that during most of the procedure, both the fully coated back side and the partially coated front side are foreclosed from supplying electrosurgical currents to the adjacent tissue. Moreover, the markings on the back side are helpful in assisting the physian during the step-by-step electrode advancement and retraction from the patient's tissue While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. An electrosurgical electrode for treatment of glaucoma, comprising:
   (a) an electrically-conductive member having a longitudinal direction and a first end for mounting to a handpiece and a second end,
   (b) said second end comprising a thin flat electrically-conductive, strip portion having a first length and terminated in a rounded end and having flat front and back sides, the rounded end at one side forming an active surface region on the front side that is bare and thus electrically active for applying electrosurgical currents to selected tissue contained in and around the eye when said electrically-conductive member is connected via its first end to a source of electrosurgical currents, the active bare surface region having a second length that is approximately 1/10–1/3 of the first length,
   (d) the remaining part of the front side and the entire back side of the strip portion being electrically-insulating to prevent contact and passage of electrosurgical currents to areas adjacent to or surrounding the selected tissue contained in and around the eye.

2. An electrosurgical electrode as claimed in claim 1, wherein the second end has a first portion adjacent the active surface region and a second portion remote from the active surface region, the electrical insulation on the back side and the remaining part of the front side being formed by electrically-insulating coatings on a brass substrate.

3. An electrosurgical electrode as claimed in claim 2, wherein the substrate is slightly flexible.

4. An electrosurgical electrode as claimed in claim 2, wherein the electrically-insulating coating on the first portion is thinner than the electrically-insulating coating on the second portion.

5. An electrosurgical electrode as claimed in claim 4, wherein the electrical insulation of the first portion is constituted by a coating having a thickness in the range of about 0.002–0.008 inches.

6. An electrosurgical electrode as claimed in claim 1, further comprisings markings on the back side for indicating penetration depth into tissue of the electrode.

7. An electrosurgical electrode as claimed in claim 6, wherein the markings are spaced evenly apart.

8. An electrosurgical electrode for treatment of glaucoma comprising:

(a) an electrically-conductive member having a longitudinal direction and a first end for mounting to a handpiece and a second end, (b) said second end comprising a thin flat electrically-conductive, strip portion having a first length and terminated in a rounded end and having flat front and back sides, the rounded end at one side forming an active surface region on the front side that is bare and thus electrically active for applying electrosurgical currents to selected tissue contained in and around the eye when said electrically-conductive member is connected via its first end to a source of electrosurgical currents, the active bare surface region having a second length that is approximately 1/10–1/3 of the first length, (d) the remaining part of the front side and the entire back side of the strip portion being electrically-insulating to prevent contact and passage of electrosurgical currents to areas adjacent to or surrounding the selected tissue contained in and around the eye, (e) the electrically-conductive member at its second end having a given thickness which, including the electrical-insulation, is about 0.005–0.009 inches.

9. An electrosurgical electrode as claimed in claim 8, wherein the thickness is about 0.006 inches.

10. An electrosurgical electrode for treatment of glaucoma, comprising:

an electrically-conductive member having a longitudinal direction and a first end for mounting to a handpiece and a second end, said second end comprising a thin flat electrically-conductive, strip portion having a first length and terminated in a rounded end and having flat front and back sides, the rounded end at one side forming an active surface region on the front side that is bare and thus electrically active for applying electrosurgical currents to selected tissue contained in and around the eye when said electrically-conductive member is connected via its first end to a source of electrosurgical currents, the active bare surface region having a second length that is approximately 1/10–1/3 of the first length, (d) the remaining part of the front side and the entire back side of the strip portion being electrically-insulating to prevent contact and passage of electrosurgical currents to areas adjacent to or surrounding the selected tissue contained in and around the eye, (e) the electrically-conductive member at its second end having a given width which, including the electrical-insulation, is about 0.07–0.09 inches.

11. An electrosurgical electrode as claimed in claim 10, wherein the width of the electrode is about 0.0078 inches.

12. An electrosurgical electrode as claimed in claim 10, wherein the electrically-conductive member at its second end has a length dimension which is about 0.6–0.9 inches.

13. An electrosurgical electrode as claimed in claim 12, wherein the electrically-conductive member at its second end has a length dimension which is about 0.783 inches.

14. An electrosurgical electrode as claimed in claim 10, wherein the electrically-conductive member at its second end has a length dimension of the active surface region which is about 0.1–0.2 inches.

15. An electrosurgical electrode as claimed in claim 14, wherein the length dimension of the active surface region is about 0.157 inches.

16. An electrosurgical electrode for treating glaucoma, comprising:

(a) an elongated thin flat slightly-flexible metal strip having first and second flat sides and having a length direction, a width transverse to the length direction, and a thickness perpendicular to the flat sides, the thickness being substantially less than its width and its length, (b) an insulating coating over the first and second sides along substantially the entire length of the flat strip except for a spade-shaped first end that is exposed on only one of the first and second sides, the spade-shaped first end being rounded, (c) means at an end of the electrode opposite to said first end for connection to a source of electrosurgical currents, (d) said spade-shaped first end that is exposed having a dimension in the length direction of about 0.1–0.2 inches and a width of about 0.07–0.09 inches for applying electrosurgical currents via the exposed side of said spade-shaped first end to selected tissue contained in and around the eye.

17. An electrosurgical electrode as claimed in claim 16, further comprising evenly-spaced markings extending in the width direction on the other of the first and second sides.

18. In combination:

i) electrosurgical apparatus capable of supplying high frequency currents, ii) an electrosurgical electrode having an electrically-conductive end for treating glaucoma, iii) a handpiece having means at one end for connection to the electrosurgical apparatus and having at its opposite end means for mounting the electrically-conductive end of the electrosurgical electrode and for supplying the high frequency currents to said electrode;

said electrode comprising:

(a) an elongated thin flat slightly-flexible metal strip having first and second flat sides and having a length direction, a width transverse to the length direction, and a thickness perpendicular to the flat sides, the thickness being substantially less than its width and its length, (b) an insulating coating over the first and second sides along substantially the entire length of the flat strip except for a spade-shaped first end that is exposed on only one of the first and second sides, (c) means at an end of the electrode opposite to said first end for mounting in said handpiece, (d) said spade-shaped first end that is exposed having a dimension in the length direction of about 0.1–0.2 inches for applying electrosurgical currents via the exposed side of said spade-shaped first end to selected tissue contained in and around the eye.

19. The combination of claim 18, wherein the high frequency currents are at a frequency exceeding 2 MHz.

20. The combination as claimed in claim 18, wherein the spade-shaped first end that is exposed has a width of about 0.07–0.09 inches.

* * * * *